United States Patent [19]

Mercer, Jr.

[11] Patent Number: 4,733,666
[45] Date of Patent: Mar. 29, 1988

[54] SURGICAL CLIP FOR CHOLANGIOGRAPHY

[75] Inventor: Leo C. Mercer, Jr., El Paso, Tex.
[73] Assignee: Texas Tech University Health Sciences Center, Lubbock, Tex.
[21] Appl. No.: 818,651
[22] Filed: Jan. 13, 1986
[51] Int. Cl.$^4$ ............................................. A61B 17/00
[52] U.S. Cl. ................................................. 128/346
[58] Field of Search ................ 128/325, 326, 346, 354

[56] References Cited

U.S. PATENT DOCUMENTS

| 183,602 | 10/1876 | Strubell | 128/346 |
|---|---|---|---|
| 3,456,965 | 7/1969 | Gajewski et al. | 128/334 C X |
| 4,112,944 | 9/1978 | Williams | 128/346 X |
| 4,227,730 | 10/1980 | Alexander et al. | 128/346 X |
| 4,449,531 | 5/1984 | Cerwin et al. | 128/326 X |
| 4,458,681 | 7/1984 | Hopkins | 128/346 |
| 4,498,903 | 2/1985 | Mathew | 128/DIG. 26 X |
| 4,558,699 | 12/1985 | Bashour | 128/346 |

FOREIGN PATENT DOCUMENTS 1088713  4/1984  U.S.S.R. .............................. 128/325

OTHER PUBLICATIONS

Padula et al., "A New Clamp for Rapid Vascular Anastomosis", *Surgery*, Jun. 1965, vol. 57, #6, pp. 819-822.

*Primary Examiner*—Michael H. Thaler
*Attorney, Agent, or Firm*—Arnold, White & Durkee

[57] ABSTRACT

A surgical clip is disclosed. The clip may be used to anchor a cholangiographic catheter that has been previously inserted into the cystic duct to the position it has been placed within the cystic duct.

3 Claims, 2 Drawing Figures

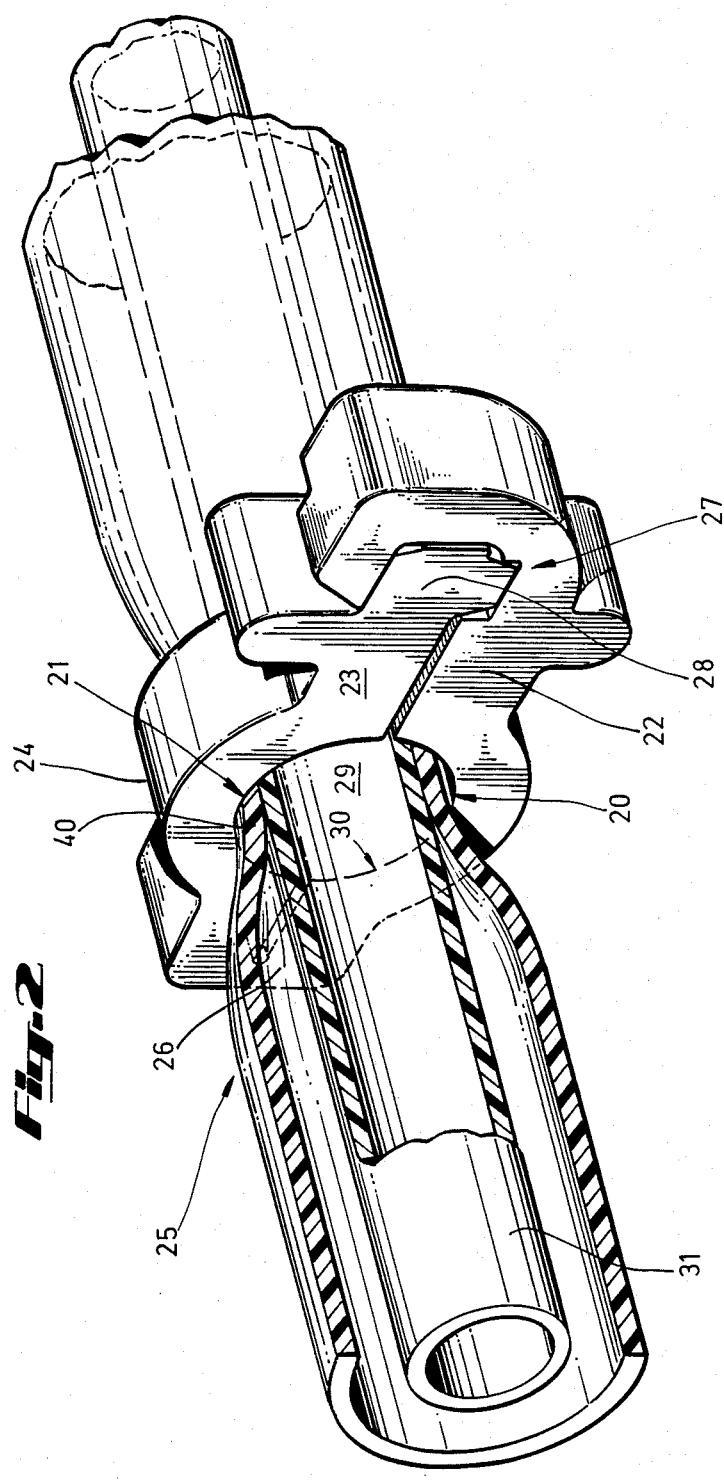

SURGICAL CLIP FOR CHOLANGIOGRAPHY

FIELD OF THE INVENTION

The present invention relates to surgical clips for anchoring tubular surgical instruments, that have been inserted into hollow linear organ structures, to the position they have been placed within these linear organ structures. The invention has particular application in anchoring a cholangiographic catheter in place within the cystic duct to facilitate trans-cystic duct cholangiography.

BACKGROUND OF THE INVENTION

Intraoperative cholangiography is the most effective means of evaluating the extrahepatic biliary ductal system at the time of cholecystectomy.

To facilitate trans-cystic duct cholangiography, catheter placement into the cystic duct should be rapid, leakproof, technically simple and allow for rapid introduction of contrast medium into the ductal system. Various techniques of holding the catheter in place within the cystic duct have been proposed and used including simple ligature, Javid clamp, a loosely applied hemoclip and a modified Rummel tourniquet.

Several disadvantages are associated with these techniques. One disadvantage is the difficulty in securing a ligature around the duct, especially in obese patients. Another disadvantage is that cumbersome equipment used in the operative field predisposes the catheter to being dislodged. Further, such techniques may crimp the catheter or cause leakage of contrast medium and radiopaque objects within the operative field. Some ligating clips (HEMOCLIP, Weck; LIGACLIP, Ethicon) cannot be easily adjusted or held in place.

The present invention provides a surgical clip that snugly anchors a catheter, previously inserted into the cystic duct, to the position it has been placed within the cystic duct.

Another advantage of the present invention is to provide a surgical clip for anchoring a catheter to the cystic duct that will not dislodge or crimp the catheter. This facilitates anchoring a catheter in place within a cystic duct without causing leakage of contrast medium and radiopaque objects within the operative field while performing intraoperative cholangiography of the extrahepatic biliary ductal system at the time of cholecystectomy.

A further advantage of the present inventive surgical clip is that is easily allows the securing of a ligature around the cystic duct for obese patients as well as other patients.

As will become apparent in the description of a preferred embodiment of the surgical clip of the present invention, the clip may be used to snugly anchor other tubular surgical instruments that have been previously inserted into other hollow linear organ structures to the position they have been placed within these structures.

Additional advantages of the invention will be set forth in part in the description which follows, and in part will be obvious from the description, or may be learned by practice of the invention.

SUMMARY OF THE INVENTION

In accordance with the present invention as embodied and broadly described herein, a surgical clip is provided for snugly anchoring a catheter in place within the cystic duct. This clip comprises two arms that are axially displaced from each other at one end and are rotatably connected to each other at the other end. Each arm possesses a generally semi-circular recessed groove cut into one side of each arm. When the axially displaced ends of each arm are connected, these grooves combine to produce a clip having a generally circular passageway extending through the clip.

This generally circular passageway compresses the outer wall of the cystic duct which, in turn, causes the inner wall of the cystic duct to snugly grip a cholangiographic catheter that has been inserted into the duct. These compressive forces inhibit the slippage of the catheter from the position it has been placed in the cystic duct. At the same time, the clip does not cause the catheter to be dislodged or crimped, or cause the leakage of contrast medium and radiopaque objects within the operative field.

DESCRIPTION OF THE DRAWINGS

FIG. 2 is a perspective view of an embodiment of the surgical clip of the invention engaged with a catheter that has been inserted into a cystic duct.

DETAILED DESCRIPTION OF PREFERRED EMBODIMENTS

Figure 1:
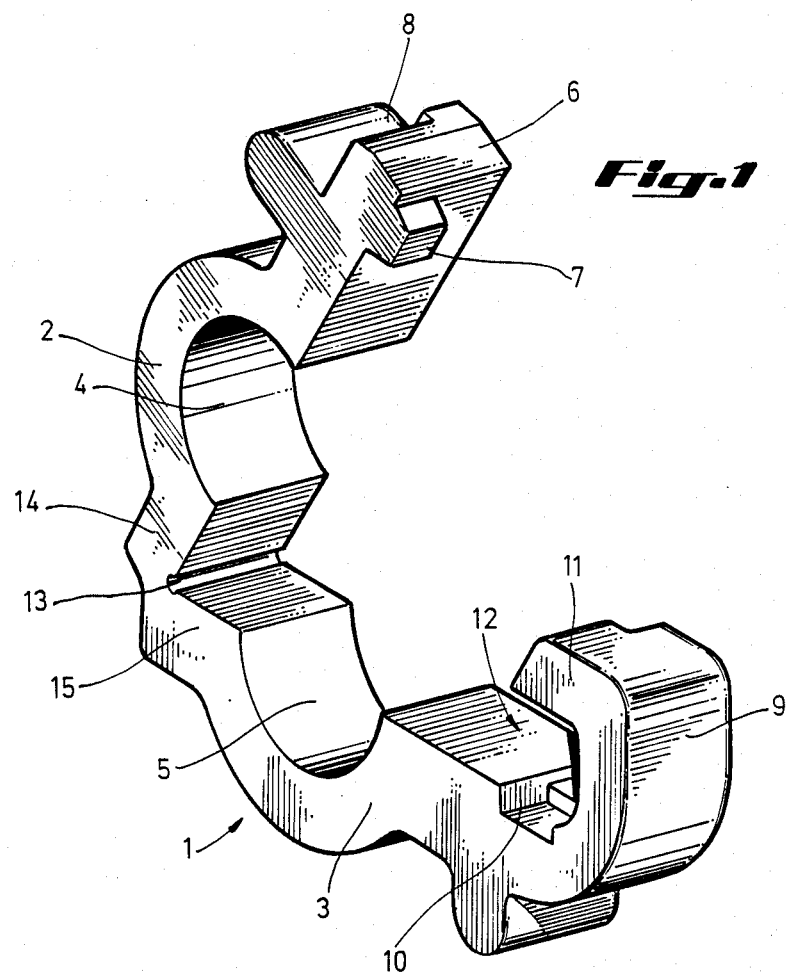
FIG. 1 is a perspective view of an embodiment of the surgical clip of the present invention.

The present invention is a surgical clip for snugly anchoring tubular surgical instruments, previously inserted into hollow linear organ structures, to the position they have been placed within these structures.

As shown in FIG. 1, a preferred embodiment of this clip 1 has two arms 2, 3 axially displaced from each other at one end and rotatably connected to each other at the other end.

A generally semi-circular recessed groove 4, 5 is cut into one side of each arm 2, 3. The axially displaced end 6 of one arm 2 possesses a lug 7 and slotted groove 8. The axially displaced end 9 of the other arm 3 has a recessed groove 10 cut into it and an inward facing flange 11, leaving a gap 12 between the recessed groove 10 and the flange 11.

The axially displaced ends 6, 9 may be locked together by rotating the arms 2, 3 about the axis of the hinge 13 that connects the joined ends 14, 15 of the arms 2, 3, until the lug 7 and slotted groove 8 of one axially displaced end 6 penetrate into the gap 12 between the recessed groove 10 and the flange 11 of the other axially displaced end 9.

The flange 11 prevents the arms 2, 3 from radially separating from each other. The insertion of the lug 7 into the recessed groove 10 helps prevent the arms 2, 3 from separating in a direction perpendicular to the plane through which the arms 2, 3 pivot around the hinge 13.

When performing intraoperative cholangiography, a catheter is placed through the cystic duct and into the common bile duct using standard surgical methods. As shown in FIG. 2, the semi-circular recessed groove 20 of one of the arms 22 of the surgical clip 24 of the present invention may be placed around the cystic duct 25. The semi-circular recessed groove 21 in the other arm 23 pivots around the hinge 26 enabling the axially displaced end 27 of one arm 22 to lock into the axially displaced end 28 of the other arm 23. One may use a standard clip applier (ABSOLOK, Ethicon) to lock the axially displaced ends 27, 28 together.

FIG. 2 shows that locking the clip 24 together produces a circular passageway 29 that extends through the clip 24. The walls 30 of this passageway 29 snugly grip the cystic duct 25. These compressive forces cause the inner walls 40 of the cystic duct 25 to snugly anchor the catheter 31 to the cystic duct 25. These forces inhibit the slippage of the catheter 31 from the position it has been placed in the cystic duct 25.

FIG. 2 shows that the clip 24 of the present invention snugly holds a catheter 31 to the cystic duct 25 without crimping the catheter 31 or causing leakage of contrast medium and radiopaque objects within the operative field.

The clip may be inserted into place quickly and easily without predisposing the catheter to being dislodged. Further, for use in intraoperative cholangiography, the clip may be made of radiolucent material that contains no opacities within the radiographic field which might obscure detail.

The clip may be made of absorbable material allowing the clip to be left on the duct at the conclusion of the cholangiographic study or the clip may be unlocked and removed. The clip may consist of different sizes for use with different sized cystic ducts. Alternatively, the semi-circular recessed grooves may be enlarged to accommodate larger cystic ducts.

The clip may be made of polydioxonone (Ethicon) or a suitable biocompatible plastic material or other material suitable for surgical use.

As is readily apparent from the design of the clip, the clip may be used for other types of surgery. The clip of the present invention may be used with any type of surgery involving the insertion of a tubular surgical instrument into a hollow linear organ structure in order to anchor the tubular surgical instrument in place within the linear organ structure.

Consequently, additional advantages and modifications will readily occur to those skilled in the art. The invention in its broader aspects is therefore not limited to the specific details, representative apparatus, and the illustrative example shown and described. Accordingly, departures may be made from the detail without departing from the spirit or scope of the disclosed general inventive concept.

What is claimed is:

1. A surgical clip of one-piece integral construction for hollow linear organ structures comprising:
   two arms axially displaced from each other at one end and rotatably connected to each other at the other end;
   said arms having substantially flat planar surfaces except for a single generally semi-circular recessed groove located on each said arm, the generally semi-circular recessed groove of one arm facing the generally semi-circular recessed groove of the other arm in a coplanar relationship, enabling the connecting of said axially displaced ends to produce a surgical clip having a generally circular passageway extending through said surgical clip substantially normal to the plane of the clip's rotation;
   one of said axially displaced ends possesses a single lug and a single slotted groove; and
   the other said axially displaced end possesses a single recessed groove and a single inward facing flange;
   said lug and slotted groove being insertable into a gap between said recessed groove and said flange, enabling said lug and slotted groove to be locked into position between said recessed groove and said flange, enabling the connection of one axially displaced end of one arm to the axially displaced end of the other arm;
   said surgical clip enabling the application of an axially distributed compressive force against said hollow linear organ structure and wherein said surgical clip is composed of a biocompatible material and is absorbable.

2. The surgical clip of claim 1 wherein said surgical clip is radiolucent.

3. The surgical clip of claim 1 wherein said surgical clip is composed of polydioxanone.

* * * * *